United States Patent [19]

Hunziker

[11] Patent Number: 4,584,251
[45] Date of Patent: Apr. 22, 1986

[54] SOLID ELECTROLYTE CELL AND IODINE-DOPED METAL COMPLEXES AS THE CATHODE MATERIAL

[75] Inventor: Max Hunziker, Basel, Switzerland

[73] Assignee: Ciba-Geigy Corporation, Ardsley, N.Y.

[21] Appl. No.: 680,682

[22] Filed: Dec. 12, 1984

[30] Foreign Application Priority Data

Dec. 23, 1983 [CH] Switzerland ............... 6884/83

[51] Int. Cl.$^4$ ........................... H01M 4/60
[52] U.S. Cl. ......................... 429/191; 429/213
[58] Field of Search ............ 429/101, 213, 191, 192, 429/43; 252/182.1

[56] References Cited

U.S. PATENT DOCUMENTS

| | | | |
|---|---|---|---|
| 3,674,562 | 7/1972 | Schneider et al. | 429/192 |
| 3,773,557 | 11/1973 | Mead | 429/192 |
| 4,049,890 | 7/1972 | Schneider | 429/192 |
| 4,340,651 | 9/1977 | Howard et al. | 429/101 |
| 4,469,763 | 9/1984 | Walsh et al. | 429/101 |

FOREIGN PATENT DOCUMENTS

| | | | |
|---|---|---|---|
| 2128842 | 12/1972 | Fed. Rep. of Germany | 429/43 |
| 2326667 | 12/1974 | Fed. Rep. of Germany | 429/43 |
| 56-30261 | 3/1981 | Japan | |

OTHER PUBLICATIONS

Max Hunziker et al., 9.Metallic Conductivity in Metal Tetraaza [14]Annulene Iodides:, Helvetica Chimica Acta, vol. 64, pp. 82–89, (1981).

Primary Examiner—Donald L. Walton
Attorney, Agent, or Firm—Michael W. Glynn; Irving M. Fishman

[57] ABSTRACT

Charge-transfer complexes of the formula I

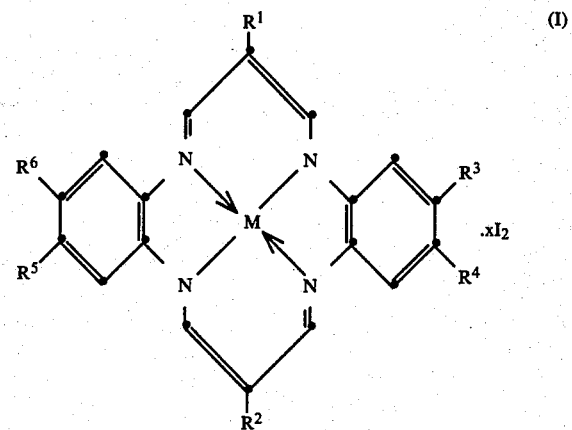

in which M, $R^1$ to $R^6$ and x are as defined in claim 1 are suitable as cathode material in lithium/iodine or silver-/iodine solid electrolyte cells.

8 Claims, 2 Drawing Figures

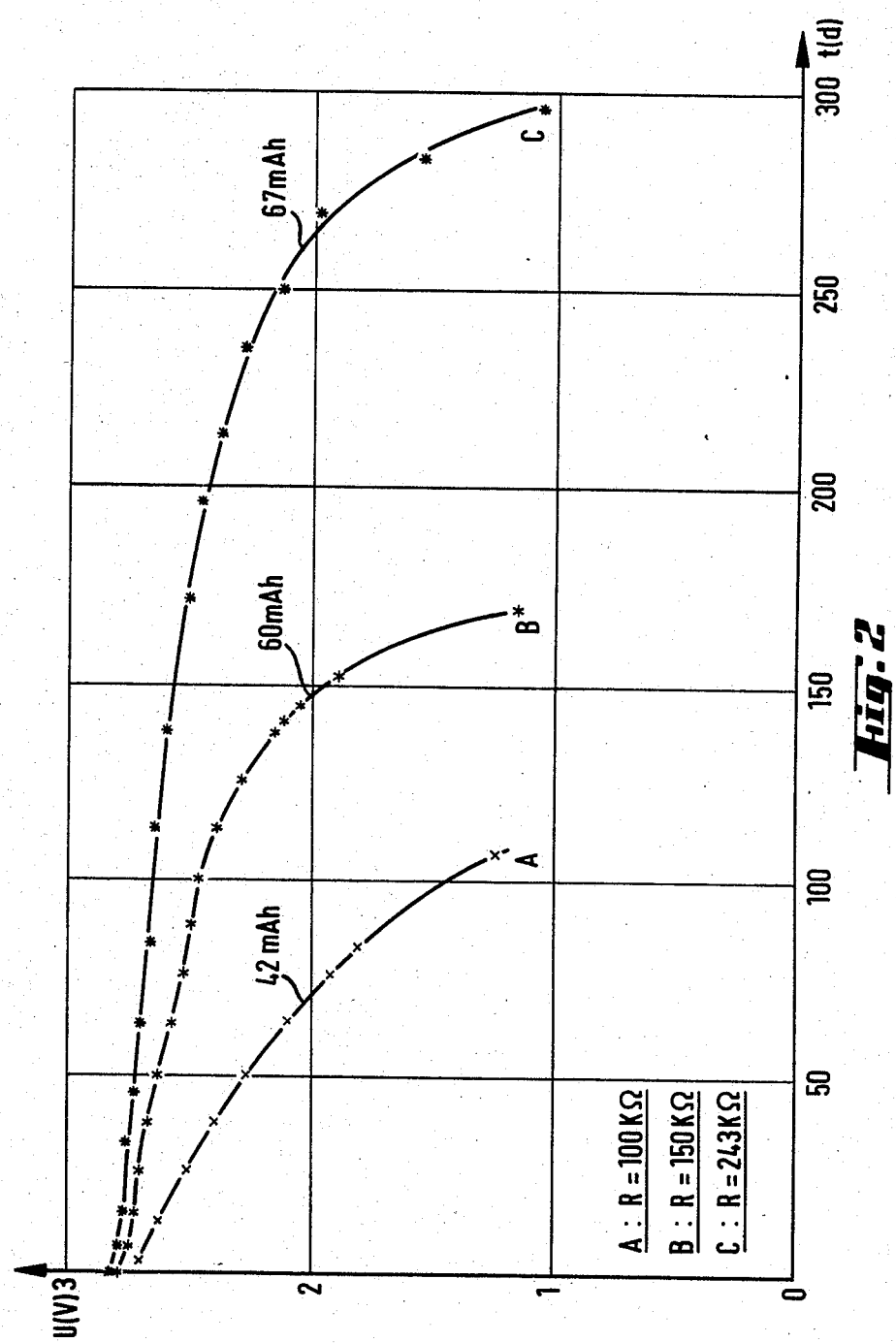

SOLID ELECTROLYTE CELL AND IODINE-DOPED METAL COMPLEXES AS THE CATHODE MATERIAL

The present invention relates to a solid electrolyte cell having solid lithium or silver as the anode, a solid lithium iodide or silver iodide as the electrolyte and an iodine-dropped dibenzotetraaza[14]annulene metal complex as the cathode material and to the metal complexes of this type and a process for their preparation.

The use of organic charge-transfer complexes as the cathode material in solid electrolyte cells is known. Iodine-doped polymers, for example polyvinylpyridine (PVP) and polyvinylquinoline (PVQ), have prove to be complexes of industrial interest. Over and above the iodine attached as a complex, these materials can additionally contain molecular iodine up to a total content of 124 moles of $I_2$ per mole of monomer (cf. U.S. Pat. No. 4,340,651).

It is mentioned in Japanese Patent Publication Sho 56-30, 261 that these materials are semi-solid to pasty and can therefore only be processed with difficulty. The tabletting of the materials in particular poses difficulties. As a rule, cathodes of PVP-$I_2$ are cast at an elevated temperature. Only at iodine contents up to not more than 30 moles of $I_2$ permole of vinylpyridine is it possible to mix the material in the solid state and to tablet it without deliquescence. However, these materials which have been mixed in the solid state from PVP and $I_2$, have high initial resistance values which take months to decrease again (cf. U.S. Pat. No. 4,148,975). The consequence of this is that solid electrolyte cells containing these cathode materials have very high initial resistance values, and only maintain a usuable potential at a slow discharge in the region of a few $\mu$A (very high load resistance values).

In the Japanese Patent Publication Sho 56-30, 261 already mentioned, charge-transfer complexes of iodine or bromine and phthalocyanine metal complexes are suggested as cathode material for lithium cells. The doping with iodine takes place very slowly either in organic solvents or using gaseous iodine, and can take up to a month. The amounts of iodine taken up are relatively small, which leads to a short working life for the batteries, which also only have a low energy density.

It has now been found that iodine-doped dibenzotetraaza[14]annulene metal complexes are excellently suitable as cathode material in lithium/iodine solid electrolyte cells. The complexes can be prepared easily, can be doped with iodine within short periods and have a high conductivity even at high iodine contents. In addition, higher energy densities are achieved, in comparison with the phthalocyanine complexes. The complexes are also observed to have, as soon as they have been prepared, only a low initial resistance value, which decreases even further in the course of short periods of time in the case of charge-transfer complexes prepared by mixing or griding the solid reactants, this decrease having, however, no appreciable effect on the internal resistance of a battery.

The present invention relates to a solid electrolyte cell containing a solid anode made of lithium or silver, a solid lithium iodide or silver iodide electrolyte and a charge-transfer complex consisting of a metal complex, and iodine as the cathode, wherein the cathode consists of an iodine-doped complex or a mixture thereof with iodine having the formula I

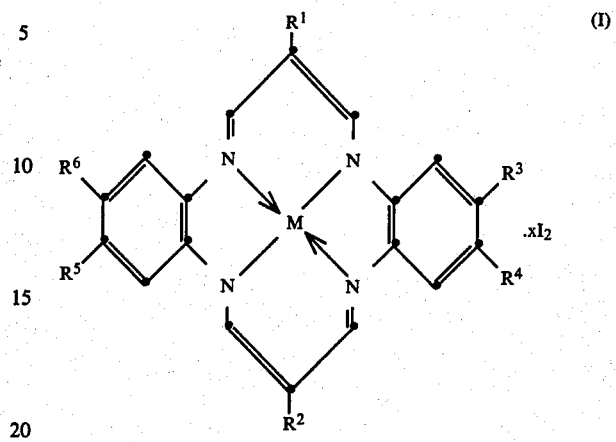

in which M is a divalent metal atom belonging to the group consisting of Fe, Co, Ni, Cu, Zn, Pd and Pt, $R^1$ and $R^2$ independently of one another are a hydrogen atom or alkyl, cycloalkyl, aryl, aralkyl, alkaralkyl or acyl each of which is unsubstituted or substituted, $R^3$, $R^4$, $R^5$ and $R^6$ independently of one another are a hydrogen atom, alkyl, alkoxy, alkylthio and alkoxycarbonyl having 1 to 8 C atoms, aryloxy or halogen, or $R^3$ and $R^4$ and also $R^5$ and $R^6$ together are $-(CH_2)_n-$ in which $n=3$, 4 or 5, $-O-(CH_2)_m-O-$ in which $m=1-4$, or a radical of the formula $-CH=CH-CH=CH-$ and x is a rational number from 1 to 300.

The complex of the formula I expresses the fact that a partial, non-integral charge transfer has taken place between the metal complex and part of the iodine and that further excess iodine can be present in a molecular form.

In formula I, M is preferably Fe and especially Cu or Ni. $R^1$ and $R^2$ are preferably identical subsituents and the same is true for $R^3$ to $R_6$.

As alkyl, $R^1$ and $R^2$ can be linear or branched and preferably contain 1 to 6, especially 1 to 4, C atoms. Examples are hexyl, pentyl, t-butyl, sec.-butyl, n-butyl, n-propyl, i-propyl and especially ethyl and methyl.

As cycloalkyl, $R^1$ and $R^2$ preferably contain 5 or 6 ring carbon atoms and can be, for example, cyclopentyl or cyclohexyl.

As acyl, $R^1$ and $R^2$ preferably contain 2 to 6, especially 2 to 4, C atoms and can be, for example, acetyl, propionyl or benzoyl. Examples of suitable substituents for $R^1$ and $R^2$ are halogen, such as Br, Cl and F, or alkoxy which preferably has 1 to 4 C atoms.

As aryl, $R^1$ and $R^2$ are preferably phenyl which can be substituted, for example, by halogen, especially Cl and F, or alkoxy having 1 to 4 C atoms, especially methoxy. The substituents are preferably located in the para-position.

As alkaryl, $R^1$ and $R^2$ are preferably alkylphenyl, especially p-alkylphenyl which preferably has 1 to 4 C atoms in the alkyl group. Examples are p-butylphenyl, p-propylphenyl, p-ethylphenyl and especially p-methylphenyl.

As alkaralkyl, $R^1$ and $R^2$ are preferably alkylbenzyl which preferably has 1 to 4 C atoms in the alkyl group, especially p-alkylbenzyl, for example p-methylbenzyl.

A preferred subgroup of the complexes of the formula I is formed by those in which $R^3$ to $R^6$ are a hydrogen atom and $R^1$ and $R^2$ are a hydrogen atom or alkyl, cycloalkyl, aryl, aralkyl, alkaralkyl or acyl.

As alkyl, alkoxy, alkylthio and alkoxycarbonyl, $R^3$ to $R^6$ preferably contain 1 to 4 C atoms and can be linear or branched. Examples are n-butyl, sec.-butyl, t-butyl, n-propyl, i-propyl, butoxy, propoxy, ethoxy, butylthio, propylthio, ethylthio, methoxycarbonyl, ethoxycarbonyl and especially methyl, ethyl, methoxy and methylthio. $R^3$ and $R^4$ and also $R^5$ and $R^6$ together are preferably $-(CH_2)_n-$, $-OCH_2O-$, $-OCH_2CH_2O-$ or $-CH=CH-CH=CH-$. As aryloxy, $R^3$ to $R^6$ are preferably phenoxy, and as halogen, they are preferably Cl and especially F.

In a preferred embodiment, $R^1$ to $R^6$ independently of one another are a hydrogen atom or one of the hydrocarbon groups previously defined, especially alkyl.

In formula I, x can preferably be a number from 1 to 200, especially 1 to 100 and particularly 2 to 50.

In a preferred embodiment, the cathode material consists of complexes of the formula I in which $R^1$ to $R^6$ independently of one another are a hydrogen atom or methyl and M is Cu or Ni.

Complexes of the formula I in which x is a number not less than 5, preferably not less than 10, are novel. In these complexes, there is an excess of iodine, so that the charge-transfer complexes are distributed within a matrix of iodine. These mixtures surprisingly also have a high conductivity and are distinguished by a low resistance value when used as cathode material in batteries.

The present invention also relates to an iodine-doped complex or a mixture thereof with iodine which has the formula II

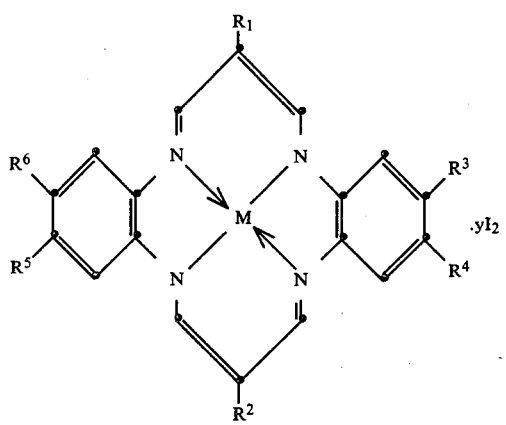

in which M is a divalent metal atom belonging to the group consisting of Fe, Co, Ni, Cu, Zn, Pd and Pt, $R^1$ and $R^2$ independently of one another are a hydrogen atom or alkyl, cycloalkyl, aryl, aralkyl. alkaralkyl or acyl each of which is unsubstituted or substituted, $R^3$, $R^4$, $R^5$ and $R^6$ independently of one another are a hydrogen atom, alkyl, alkoxy, alkylthio and alkoxycarbonyl having 1 to 8 C atoms, aryloxy or halogen, or $R^3$ and $R^4$ and also $R^5$ and $R^6$ together are $-(CH_2)_n-$ in which n=3, 4 or 5, $-O-(CH_2)_m-O-$ in which m=1 to 4, or a radical of the formula $-CH=CH-CH=CH-$, and y is a rational number from 5 to 300.

The same preferences as for the complexes of the formula I apply to the complexes of the formula II. The number y is preferably 5 to 200, especially 5 to 100 and particularly 5 to 50. The number y (as also the number x in formula I) indicates the molar ratio of metal complex to molecular iodine.

The preparation of the iodine-doped complexes or mixtures thereof with iodine having the formulae I and II is effected in a manner known per se by oxidising a metal complex of the formula III

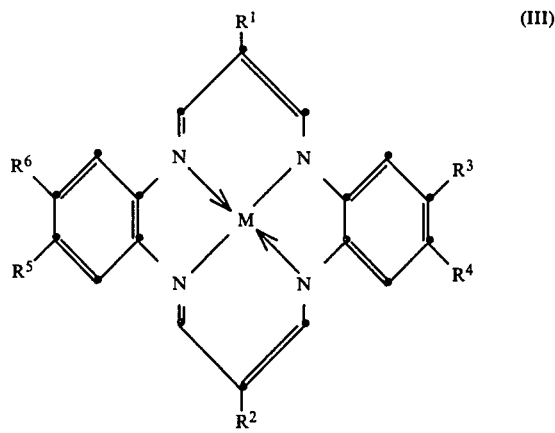

in which M and $R^1$ to $R^6$ are as defined above, by means of x or y moles of molecular iodine and, if appropriate, subsequently mixing the resulting charge-transfer complexes with iodine.

The metal complexes of the formula III are known [Helvetica Chimica Acta, Volume 64, Issue 8, pages 2544–2554 (1981)] or can be prepared by analogous processes. Charge-transfer complexes having up to 4 moles of molecular iodine are also described therein.

The oxidation is preferably carried out under an atmosphere of a protective gas and with the exclusion of moisture. Various embodiments are possible for the oxidation by means of iodine. Iodine vapour can be allowed to act at room temperature on a solid metal complex of the formula III until no further absorption of iodine takes place, or the two components can be reacted with one another in the gaseous state at an elevated temperature in a co-sublimation process. It is more advantageous to carry out the oxidation in suitable inert solvents, preferably in polar, aprotic organic solvents. In general, this process gives charge-transfer complexes which have a definite stoichiometry and a crystalline to pulverulent form and which can have a molar ratio of metal complex to molecular iodine of up to about 1:8.

In order to achieve higher iodine contents, the charge-transfer complexes thus obtained can be mixed with iodine in the desired ratio, for example in customary mixers equipped with high-speed stirring equipment, and advantageously in the melt at high iodine contents. In the case of dry powders, perparation by intensive grinding is also possible.

It is simpler to mix the metal complexes of the formula III directly with iodine in the desired ratio; this is preferably carried out under an atmosphere of a protective gas and with the exclusion of moisture. Up to an iodine content of about 20 moles of molecular iodine per mole of metal complex of the formula III, mixing by, for example, intensive grinding is possible, since solid, pulverulent products are formed. At higher iodine contents, the behaviour of the solid lid is increasingly determined by the soft, plastic iodine, and the mixing is more advantageously carried out in the melt. The reaction times required for the formation of the charge-transfer complexes are within the range from minutes to a few hours, which is very efficient from the economic point of view.

The charge-transfer complexes or mixtures thereof with iodine having the formulae I and II are black solids which have an electrical conductivity within the range from $10^{-1}$ to about $10^{-4}$ S cm$^{-1}$. They can be processed easily and are excellently suitable for use as cathode material in lithium/iodine or silver/iodine solid electrolyte cells (batteries).

The batteries can be constructed in various shapes, for example as button cells, as flat foil batteries or cylindrical batteries or in the form of fairly large batteries which can also contain several cells. The batteries consist of a can of electrically conducting material which is inert towards the cathode material. This can be metals or metal alloys, for example stainless or chrome-nickel steel. The lid of the battery also consists of such materials. The anode, consisting of lithium or silver, and the cathode, consisting of the complexes of the formula I, are located between the lid and the can. The solid electrolyte layer, consisting of LiI or AgI, develops of itself into an intermediate layer as a result of connecting the anode and cathode. The lid and can are sealed by means of a suitable sealing composition, for example a composition made of plastics, such as polypropylene.

FIG. 2 shows the discharge curves of 3 button cells at different rates of current supply; (dbtaa) represents dibenzotetraazaannulene.

Figure 1:
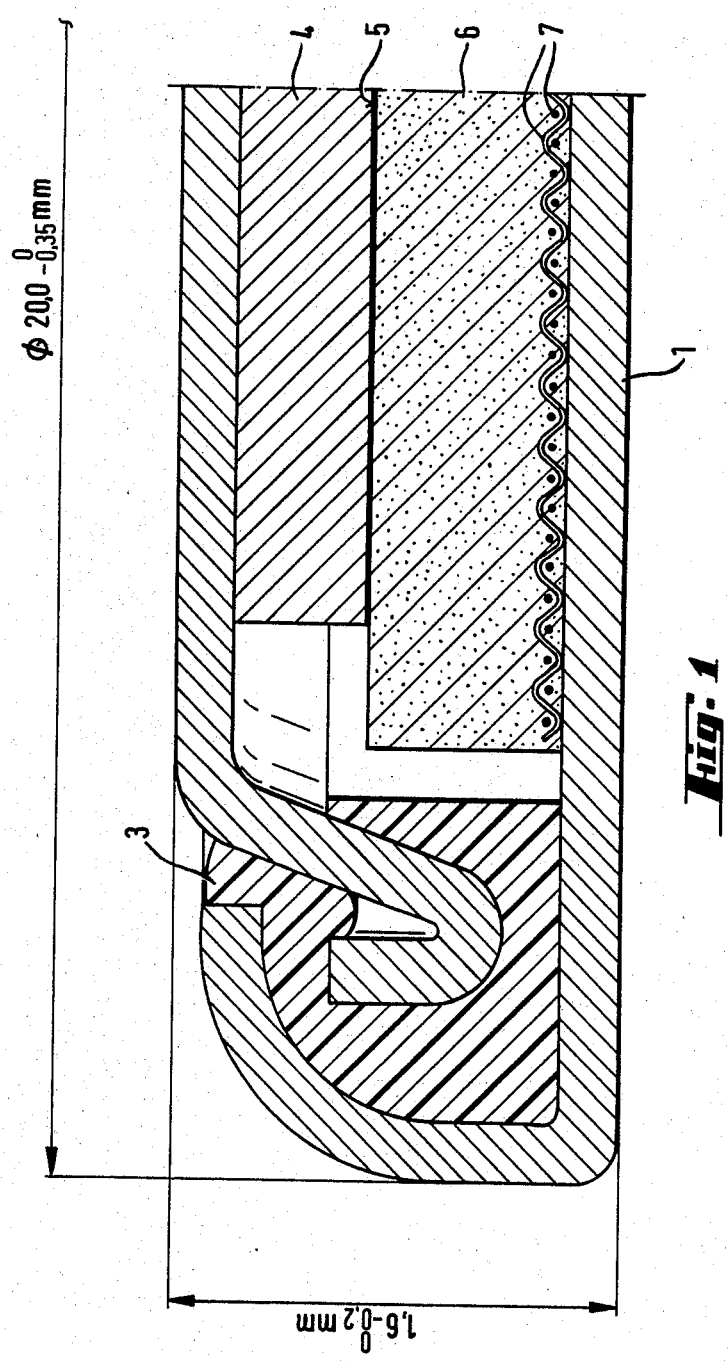
FIG. 1 shows a partial view of a battery constructed in the form of a button cell.

The batteries are prepared in a known manner by assembling the individual constitutents with the application of pressure under an atmosphere of a protective gas and with the exclusion of moisture.

The cathodes can be prepared in a known manner, for example by compressing the iodine-doped complexes or mixtures thereof with iodine having the formula I to give, for example, tablets or other shapes. Dry powders are particularly suitable for this process. It is therefore preferable to use charge-transfer complexes having an iodine content of 2 to 50, especially 2 to 20, moles of molecular iodine per mole of metal complex of the formula III. Conductive materials which improve the electrical contact between the can and the cathode, for example wire netting made of metals, can be concomitantly incorporated into the cathode and can also be spot-welded to the can. The charge-transfer complexes of the formula I and mixtures thereof with iodine can also be employed as a casting composition for the production of various shapes of cathode.

The batteries according to the invention are distinguished by a relatively long working life. A conceivable destruction caused by iodine, observable by exudation of iodine, is not found over a prolonged period of time. The potential achievable (open-circuit voltage, OCV) is 2.8 V and the internal resistance values for button cells of size 2016 in the non-discharged state are approximately between 0.2 and 1.2 kil ohms.

The batteries according to the invention can be used for the operation of electrical equipment having a low current consumption. In the form of button batteries they can be employed in electronic clocks or electric calculators, for example as a memory back-up.

The following examples illustrate the invention in greater detail.

(A) PREPARATION EXAMPLES 1-15

The charge-transfer complexes described in Table 1 below are prepared by the following methods:

(a) Preparation by mixing in an iodine melt 1.7 g of metal complex of the formula III and iodine corresponding to the molar ratios indicated in Table 1 are put into a 0.3 litre glass insert in an autoclave, with the exclusion of moisture and under argon, and the autoclave is closed. Stirring is then carried out for 1 hour and the melt is then cooled.

(b) Preparation by mixing the components in powder from 5 g of metal complex of the formula III and iodine corresponding to the molar ratios in Table 1 are mixed, with the exclusion of water, in a laboratory mixer for 2 minutes at full revolution. The conductivity values after storage for 3 days are shown in Table 1.

TABLE 1

| Example No. | Method of preparation | Metal complex of the formula III (A) | | | | | | | Molar ratio A:I$_2$ | Conductivity at 25° C. (S cm$^{-1}$) |
|---|---|---|---|---|---|---|---|---|---|---|
| | | M | R$^1$ | R$^2$ | R$^3$ | R$^4$ | R$^5$ | R$^6$ | | |
| 1 | b | Ni | H | H | H | H | H | H | 1:10 | $1 \times 10^{-2}$ |
| 2 | b | Ni | H | H | H | H | H | H | 1:20 | $3 \times 10^{-3}$ |
| 3 | a | Ni | H | H | H | H | H | H | 1:53.2 | $2,5 \times 10^{-3}$ |
| 4 | b | Ni | CH$_3$ | CH$_3$ | H | H | H | H | 1:10 | $1 \times 10^{-3}$ |
| 5 | a | Ni | CH$_3$ | CH$_3$ | H | H | H | H | 1:65.6 | $9,4 \times 10^{-4}$ |
| 6 | a | Ni | H | H | CH$_3$ | H | CH$_3$ | H | 1:53.2 | $1,7 \times 10^{-4}$ |
| 7 | a | Ni | CH$_3$ | CH$_3$ | CH$_3$ | H | CH$_3$ | H | 1:75.5 | $9,6 \times 10^{-4}$ |
| 8 | a | Ni | CH$_3$ | CH$_3$ | CH$_3$ | CH$_3$ | CH$_3$ | CH$_3$ | 1:113.3 | $1,6 \times 10^{-3}$ |
| 9 | a | Ni | p-Toluyl | H | H | H | H | H | 1:88.3 | $7 \times 10^{-4}$ |
| 10 | a | Cu | H | H | H | H | H | H | 1:21.8 | $3,3 \times 10^{-3}$ |
| 11 | b | Fe | CH$_3$ | CH$_3$ | H | H | H | H | 1:20.4 | $4,5 \times 10^{-2}$ |
| 12 | a | Ni | H | H | —CH=CH—C=CH— | | —CH=CH—CH=CH— | | 1:44.8 | $4 \times 10^{-4}$ |
| 13 | a | Ni | H | H | H | H | H | H | 1:200 | $2 \times 10^{-5}$ |
| 14 | b | Ni | H | H | —OCH$_2$CH$_2$O— | | —OCH$_2$CH$_2$O— | | 1:20 | $2 \times 10^{-4}$ |
| 15 | b | Ni | CH$_3$ | CH$_3$ | —OCH$_2$O— | | —OCH$_2$O— | | 1:20 | $1 \times 10^{-4}$ |

(B) USE EXAMPLES 16-25

The complexes of the formula I or mixtures with iodine listed in Table 2 below are prepared by method a (Examples 16 and 17) and by method b (Examples 14, 15 and 18-23) and are compressed under a pressure of 147 Mpa to give pellets of diameter 15.9 mm amd thickness 0.8 mm. A grid of stainless steel is then pressed into place under the same pressure. Button cells of thickness 1.6 mm and diameter 20 mm are then prepared in accordance with the design of FIG. 1 attached.

The cathode can and the anode lid each consist of stainless steel 0.2 mm thick. The lithium anode is punched out of foil 0.45 mm thick. The button cell is sealed by means of a seal composed of polypropylene. The preparation of the button cell is carried out under argon as a protective gas.

Table 2 shows the potential and the internal resistance value $R_i$ of the cell in the non-discharge state, as well as the composition of the cathode material.

TABLE 2

| Example No. | \multicolumn{7}{c}{Metal complex of the formula I} | OCV (volts) | $R_i$ (kΩ) |
| --- | --- | --- | --- | --- | --- | --- | --- | --- | --- |
|  | M | $R^1$ | $R^2$ | $R^3$ | $R^4$ | $R^5$ | $R^6$ | x |  |  |
| 16 | Ni | H | H | H | H | H | H | 10 | 2.806 | 0.434 |
| 17 | Ni | H | H | H | H | H | H | 10 | 2.804 | 0.587 |
| 18 | Ni | H | H | H | H | H | H | 50 | 2.806 | 0.726 |
| 19 | Ni | H | H | H | H | H | H | 50 | 2.802 | 1.02 |
| 20 | Ni | $CH_3$ | $CH_3$ | H | H | H | H | 5 | 2.804 | 0.691 |
| 21 | Ni | $CH_3$ | $CH_3$ | H | H | H | H | 5 | 2.803 | 0.725 |
| 22 | Ni | $CH_3$ | $CH_3$ | H | H | H | H | 10 | 2.806 | 0.902 |
| 23 | Ni | $CH_3$ | $CH_3$ | H | H | H | H | 10 | 2.805 | 0.732 |
| 24 | Ni | $CH_3$ | $CH_3$ | H | H | H | H | 20 | 2.807 | 0.351 |
| 25 | Ni | $CH_3$ | $CH_3$ | H | H | H | H | 20 | 2.809 | 0.247 |

What is claimed is:

1. A solid electrolyte call containing a solid anode made of lithium or silver, a solid lithium iodide or silver iodide electrolyte and a charge-transfer complex consisting of a metal complx, and iodine as the cathode, wherein the cathode consists of an iodine-doped complex or a mixture thereof with iodine having the formula I

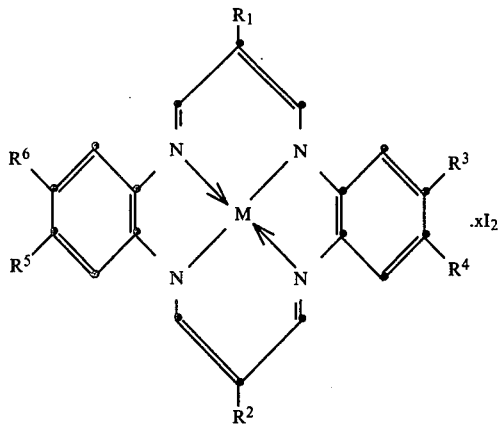

in which M is a divalent metal atom belonging to the group consisting of Fe, Co, Ni, Cu, Zn, Pd and Pt, $R^1$ and $R^2$ independently of one another are a hydrogen atom or alkyl, cycloalkyl, aryl, aralkyl, alkaralkyl or acyl each of which is unsubstituted or substituted, $R^3$, $R^4$, $R^5$ and $R^6$ independently of one another are a hydrogen atom, alkyl, alkoxy, alkylthio and alkoxycarbonyl having 1 to 8 C atoms, aryloxy or halogen, or $R^3$ and $R^4$ and also $R^5$ and $R^6$ together are $-(CH_2)_n-$ in which n=3, 4 or 5, $-O(CH_2)_mO-$ in which m=1 to 4 or a radical of the formula $-CH=CH-CH=CH-$, and x is a rational number from 1 to 300.

2. A solid electrolyte cell according to claim 1, wherein in M in formula I is Fe and especially Cu or Ni.

3. A solid electrolyte cell according to claim 1, wherein $R^1$ and $R^2$ in formula I contain 1 to 6 C atoms as alkyl, 5 or 6 ring carbon atoms as cycloalkyl and 1 to 6 C atoms as acyl, and, as aryl are phenyl, as alkaryl are alkylphenyl and as alkaralkyl are alkylbenzyl.

4. A solid electrolyte cell according to claim 1, wherein $R^1$ and $R^2$ are a hydrogen atom, methyl, ethyl, phenyl, p-methylphenyl, p-methoxyphenyl p-chlorophenyl or p-fluorophenyl and $R^3$, $R^4$, $R^5$ and $R^6$ are a hydrogen atom, methyl, ethyl, methoxy, methylthio or fluorine or $R^3$ and $R^4$ and also $R^5$ and $R^6$ together are $-(CH_2)_4-$, $-OCH_2O-$, $-OCH_2CH_2O-$ or $-CH=CH-CH=CH-$.

5. A solid electrolyte cell according to claim 1, wherein x in formula I is a number from 1 to 200, escpecially 1 to 100.

6. A solid electrolyte cell according to claim 5, wherein x in formula I is a number from 2 to 50.

7. A solid electrolyte cell according to claim 1, wherein $R^1$ to $R^6$ in formula I are a hydrogen atom or methyl and M is Cu or Ni.

8. An iodine-doped complex or mixtures thereof with iodine having the formula II

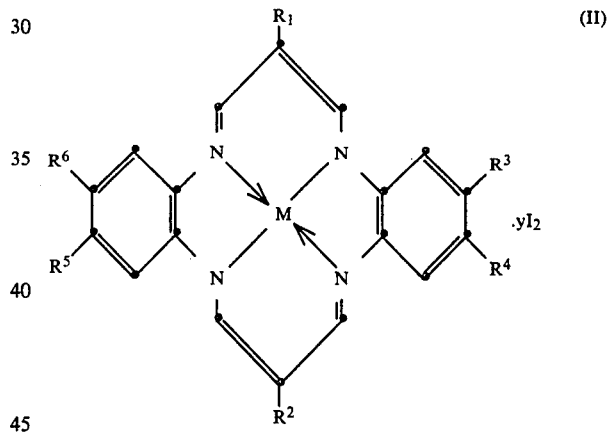

in which M is a divalent metal atom belonging to the group consisting of Fe, Co, Ni, Cu, Zn, Pd and Pt, $R^1$ and $R^2$ independently of one another are a hydrogen atom or alkyl, cycloalkyl, aryl, aralkyl, alkaralkyl or acyl each of which is unsubstituted or substituted, $R^3$, $R^4$, $R^5$ and $R^6$ independently of one another are a hydrogen atom, alkyl, alkoxy, alkylthio and alkoxycarbonyl having 1 to 8 C atoms, arloxy or halogen, or $R^3$ and $R^4$ and also $R^5$ and $R^6$ together are $-(CH_2)_n$ in which n=3,4 or 5, $-O(CH_2)_mO-$ in which m=1 to 4 or a radical of the formula $-CH=CH-CH=CH-$, and y is a rational number from 5 to 300.

* * * * *